United States Patent
Darehbidi et al.

(10) Patent No.: US 8,209,133 B2
(45) Date of Patent: Jun. 26, 2012

(54) RAPID DETERMINATION OF FATIGUE FAILURE BASED ON TEMPERATURE EVOLUTION

(75) Inventors: Mehdi Amiri Darehbidi, Baton Rouge, LA (US); Michael M. Khonsari, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 1000 days.

(21) Appl. No.: 12/221,103

(22) Filed: Jul. 31, 2008

(65) Prior Publication Data

US 2009/0048788 A1    Feb. 19, 2009

Related U.S. Application Data

(60) Provisional application No. 60/956,292, filed on Aug. 16, 2007.

(51) Int. Cl.
*G06F 19/00*      (2011.01)
(52) U.S. Cl. .............. 702/34; 702/33; 702/99; 702/130; 702/132; 702/136; 702/194; 703/2
(58) Field of Classification Search .................... 702/33, 702/34, 99, 130, 132, 136, 194; 703/2
See application file for complete search history.

(56) References Cited

OTHER PUBLICATIONS

David Broek, "Elementary Engineering Fracture Mechanics",1982 Martinus Nijhoff Publishers, p. 3-23.
G. Gargione, A. Geraci, G. La Rosa, A. Risitano, "Rapid Determination of the Fatigue Curve by the Thermographic Method", International Journal of Fatigue, 24 (2002) 11-19.
Hsin Wang, Liang Jiang, P.K. Liaw, C.R. Brooks, and D. L. Klarstrom, "Infrared Termperature Mapping of Ultimet Alloy During High-Cycle Fatigue Test", 2000, Metallurgical & Materials Transactions A, vol. 31A, Apr. 2000, p. 1307-1310.
P. K. Liaw, H. Want, L. Jian, B. Yang, J.Y. Huang, R.C. Kuo, & J.G. Huang, "Thermographic Detection of Fatigue Damage of Pressure Vessel Steels at 1,000 Hz and 20 Hz", 2000, Scripta Materialia, Scripta Mater, 42 (2000) p. 389-395, 2000 Acta Metallurgica Inc. Published by Elsevier Science Ltd.
R. Btotny, J. Kaleta, W. Grzebien and W. Adamczewski, "A Method for Determining the Heat Energy of the Fatigue Process in Metals Under Uniaxial Stress, Part 2. Measurement of 1986 the Temperature of a Fatigue Specimen by Means of Thermovision Camera—Computer System",Int J Fatigue 8 No. 1 (1986) p. 35-38, 1986 Butterworth & Co (Publishers) Ltd.
B. I. Sandor, D. T. Lohr, and K.D. Schmid, "Nondestructive Testing Using Differential Infrared Thermography", Material Evaluation/45/ Apr. 1987, p. 392-395.

(Continued)

*Primary Examiner* — Sujoy Kundu

(57) ABSTRACT

A method and apparatus are disclosed for predicting the service life of a metallic structure subjected to cyclic loading. Such structures experience fatigue, which can lead to failure after a number of loading cycles. The disclosed invention allows for an accurate prediction of the number of cycles to failure for a metallic structure by observing the slope of the rise in surface temperature of the structure after the cyclic loading has begun. The method of this invention provides early and accurate predictions of service life and does not require destructive testing. The method and apparatus of the present invention may be installed on working equipment, thus providing service life predictions for materials in real world use. The invention uses an empirically derived relationship that was confirmed using analytical relationships and material properties. The derived formula uses two constants that may be determined empirically using a disclosed process. The constants also may be estimated mathematically. The apparatus may include a wireless temperature sensor mounted on the metallic structure of interest and a data analysis unit to perform the needed calculations.

22 Claims, 16 Drawing Sheets

OTHER PUBLICATIONS

R. Attermo & G. Osthberg, "Measurements of the Temperature Rise Ahead of a Fatigue Crack", Int. Journ. of Fracture Mech., 7 (1971) p. 122-124.

D.T. Lohr, N.F. Enke, and B.I. Sandor: Dynamic Failure: Proc. 1987 Society for Experimental Mechanics (SEM) Fall Conf., Savannah, GA, Oct. 25-26, 1987, SEM, Brookfield Center, CT, p. 139-174.

T. Gross: Ph.D. Thesis: Northwestern University, Evanston, IL 1981.

M.P. Luong: Nucl. Eng. Design, 1994, vol. 158, p. 363-376.

M.P. Luong: Mech. Mater., 1998, vol. 28, p. 155-163.

J.A. Charles, F.J. Appl, and J.E. Francis: Trans. ASME, 1978, vol. 100 (4), p. 200-203.

Y. Huang, S.X. Li, S.E. Lin, and C.H. Shih: Mater. Eval. 1984, vol. 42 (7), p. 1020-1024.

M. Necati Ozisik, "Boundary Value Problems of Heat Conduction", 2002, Dover Publications.

J.D. Morrow, "Cyclic Plastic Strain Energy and Fatigue of Metals", Internal Friction, Damping, and Cyclic Plasticity, ASTM STP 378, 1965, p. 45-84.

D.Y. Tzou, "Deformation Induced Degredation of Thermal Conductivity in Cracked Solid," J. Composite Materials, vol. 28, 1994, p. 886-901.

RAPID DETERMINATION OF FATIGUE FAILURE BASED ON TEMPERATURE EVOLUTION

PRIORITY CLAIM UNDER 35 U.S.C. §119(e)

This application claims the benefit of U.S. Provisional Application No. 60/956,292, filed on Aug. 16, 2007.

FIELD OF THE INVENTION

The invention relates to materials science and engineering, and in particular to the prediction of the service life of a metallic structure exposed to cyclic loading.

BACKGROUND OF THE INVENTION

All structures and machinery components undergoing fatigue loading are prone to crack formation and its subsequent growth that increases with time. When a crack is formed, the strength of the structure or the component is decreased and can no longer function in the intended manner for which it was designed for. Moreover, the residual strength of the structure decreases progressively with increasing crack size. Eventually, after a certain time the residual strength becomes so low that the structure fails [1]. It is, therefore, of paramount importance to be able to predict the rate of decline in the component's residual strength and the remaining life of the system.

Fracture mechanics is a branch of science that provide insights into the mechanism of failure and help predict the service life of structures and machinery components [1]. As depicted in FIG. 1, several disciplines are involved in the development of fracture mechanics. At the right end of the scale is the engineering load-stress analysis. Applied mechanics covers the analysis of crack tip stress fields as well as the elastic and plastic deformations of the material in the vicinity of the crack. Material science concerns itself with the fracture processes on the scale of atoms and dislocations in the form of impurities and grains.

In order to make a successful use of fracture mechanics in an engineering application, it is essential to have some knowledge of the total field shown in FIG. 1. Fatigue failure can occur only if—as a result of the presence of micro-cracks, local yielding, micro-cavities, etc.—the applied load produces an increase in the stress in a point (or a zone) of the material, with local values exceeding the elastic limit [2]. It is known that if the stress is static, the local plasticization and the redistribution of the stress onto the surrounding material does not generate any particularly critical condition and the material reaches failure only under decidedly greater loads. On the contrary, in the case of cyclic loading, where the stress is one of fatigue, the material arrives at the condition of local yielding (micro-plasticization) and a micro-crack is generated. Hence, the repeated application of the stress leads to the crack propagation until, eventually, the condition of failure is reached and the specimen breaks.

The thermoelastic effect, which governs the relationship between the temperature variation and stress (or strain) change in the elastic range, has been well documented, and has been utilized to characterize the elastic stress field. Different means—such as thermocouples, thermistors, and thermography techniques—have been employed to monitor the temperature changes during mechanical tests [3-6]. The thermoelastic stress analysis by thermography is now an advanced full-field stress measurement method. In materials undergoing cyclic loading, most of the dissipated energy due to hysteresis effects manifests itself as heat, and the heat is removed from the material by heat transfer.

Heat can be transferred by three processes: conduction, convection, and radiation. Conduction is the transfer of heat along a solid object. Convection transfers heat from the "wetted area" of a solid through the exchange of hot and cold molecules, e.g., air, water, etc. Radiation is the transfer of heat via electromagnetic (usually infrared, IR) radiation. Although these three processes can occur simultaneously, it is not unusual for one mechanism to overshadow the other two. If the fatigue experiment is rapid enough, which is generally true for low-cycle fatigue testing, the temperature rise can be surprisingly high. For fatigue tests at 1,000 Hz, for example, the temperature could increase 200° to 400° K. above the initial temperature, depending on the material tested and specimen geometry [3, 4].

The temperature evolution resulting from the heat generated during the fatigue process is utilized to monitor the fatigue-crack propagation [5-8], to measure the energy required to produce a unit area of a fatigue crack by propagation [8], to determine the endurance limit of some materials [10, 11], and to characterize the evolution of cumulative damage in the fatigue process [3, 4, 12, 13].

In the present invention, a novel approach of nondestructive thermographic technique is used to characterize the fatigue behavior of metals. Specially, laboratory tests were conducted with Aluminum alloy and Stainless Steel undergoing cyclic bending and torsion loads. The same trend is expected to persist in multiaxial loading involving the combination of bending, tension and compression as well as torsion. In the laboratory tests, detailed temperature distributions on the specimen surface, and temperature changes as a function of time (cycles) were obtained. A two-dimensional form of a thermal-mechanical coupling model for a low-cycle bending fatigue was formulated to ensure the validity of the experimental results and to provide insight into the complex fatigue behavior. The results of the experimental and analytical works were used to develop a new method for predicting the fatigue life. The predictions of temperature changes during fatigue were found to be in good agreement with the experimental results.

In materials undergoing cyclic loading, most of the dissipated energy due to hysteresis effect manifests itself as heat and causes an increase in the mean temperature. An abrupt temperature rise in the first few cycles, followed by a steady state in later cycling, is a characteristic of metals that undergo the high-stress level fatigue testing.

In particular, we have determined that slope of the temperature-versus-time curve at the beginning of the test can be effectively utilized as an index for fatigue life prediction. This invention is expected to be applicable for the axial tension/compression loading and torsion of solid specimens of variety of shapes, as well as a thin-walled tube. Therefore, a temperature sensor, either contacting (e.g., thermocouple) or non-contacting (e.g., fiber optic, IR camera), can be used to measure the surface temperature of the specimen under cyclic loading. Test results obtained using the invention used a non-contacting sensor. In this arrangement, the need for measuring the dissipation energy due to plastic deformation from the hysteresis loop is eliminated. Also, this invention can provide an early prediction of the service life of machinery components under cyclic loading. The material properties and thermal boundary conditions are the input parameters and the service life time of the specimen is the output. Furthermore, for a system already in service, this device enables us to determine the remaining life.

Laboratory experimental results conducted at the Center for Rotating Machinery at Louisiana State University have confirmed the validity of this invention for the case of cyclic bending and torsion loads. A thermographic technique that utilizes an IR-camera (i.e., non-contacting method) was used to measure the temperature increase in the specimen due to hysteresis heating during fatigue testing. Similar results can be obtained using fiber optic temperature sensors where temperature can be recorded from a machine remotely.

A miniature electronic chip may be attached to the surface of a specimen under cyclic loading to measure its temperature and process the data to predict the onset of catastrophic failure. This device will be capable of measuring the slope of the temperature curve at the very early stages of the cyclic loading and rapidly estimate the specimen's fatigue life. For a new component, this information would pertain to the fatigue life; for an existing machine in service, it would provide estimate of the remaining life. This instrument provides a very fast and reliable method for the determination of the service life of the machinery components under cyclic loading and torsion. In practical applications, wireless technology provides compact, lightweight, reliable data transfer from the device that can be remotely monitored and processed in real time to predict the number of cycles for fatigue failure. An illustration showing the use of a wireless sensor and a data acquisition unit is shown in FIG. 2.

SUMMARY OF THE INVENTION

The surface temperature is related to the number of cycles to failure. In particular, we have determined that the slope of the temperature curve at the beginning of the test can be effectively utilized as an index for fatigue life prediction. Using this technique, the remaining life of a machine can be predicted and catastrophic failure can be avoided. This technique can be applied by installing a sensor, in-situ, and testing the component while it is undergoing the fatigue load. The life expectancy estimate is obtained while the object is in use, which provides an advantage over techniques that require stopping the operation of the machine.

It is expected that this invention is applicable to other types of loadings like axial tension/compression loading, repeated bending and torsion of thin-walled tube.

Also, it is expected that a miniature wireless temperature sensor attached to the surface of the component under the fatigue load can be used to take data and the results can be monitored remotely. In this fashion, temperature of the component is collected and at the same time transferred to a signal receiver. Other types of temperature sensors either contacting (e.g., thermocouple) or non-contacting (e.g., fiber optic, IR camera) can be used to measure the temperature of the surface of specimen under fatigue loading.

A data analyzer unit to convert the temperature data to fatigue-life span. Such a unit could calculate the slope of the temperature evolution at the beginning of the test and then convert the data to determine the service life of the component. This device may consist of an integrated electronic circuit which is programmed to process the temperature data. Processing the temperature data by this device may be carried out at the same time as the component is under the fatigue life. This type of arrangement is illustrated schematically in FIG. 2.

In a preferred embodiment, the present invention is a method of predicting the service life of an object subject to cyclic loading, including monitoring the surface temperature of the object; determining the slope ($R_\theta$) of the increase in surface temperature of the object during a first phase, wherein the first phase is defined as a period of relatively rapid increase in surface temperature of the object; and, predicting the service life of the object in number of cycles to failure ($N_f$) using the equation:

$$2N_f = c_1 R_\theta^{c_2}, \text{ wherein } c_1 \text{ and } c_2 \text{ are constants.}$$

DETAILED DESCRIPTION OF THE INVENTION

Figure 1:
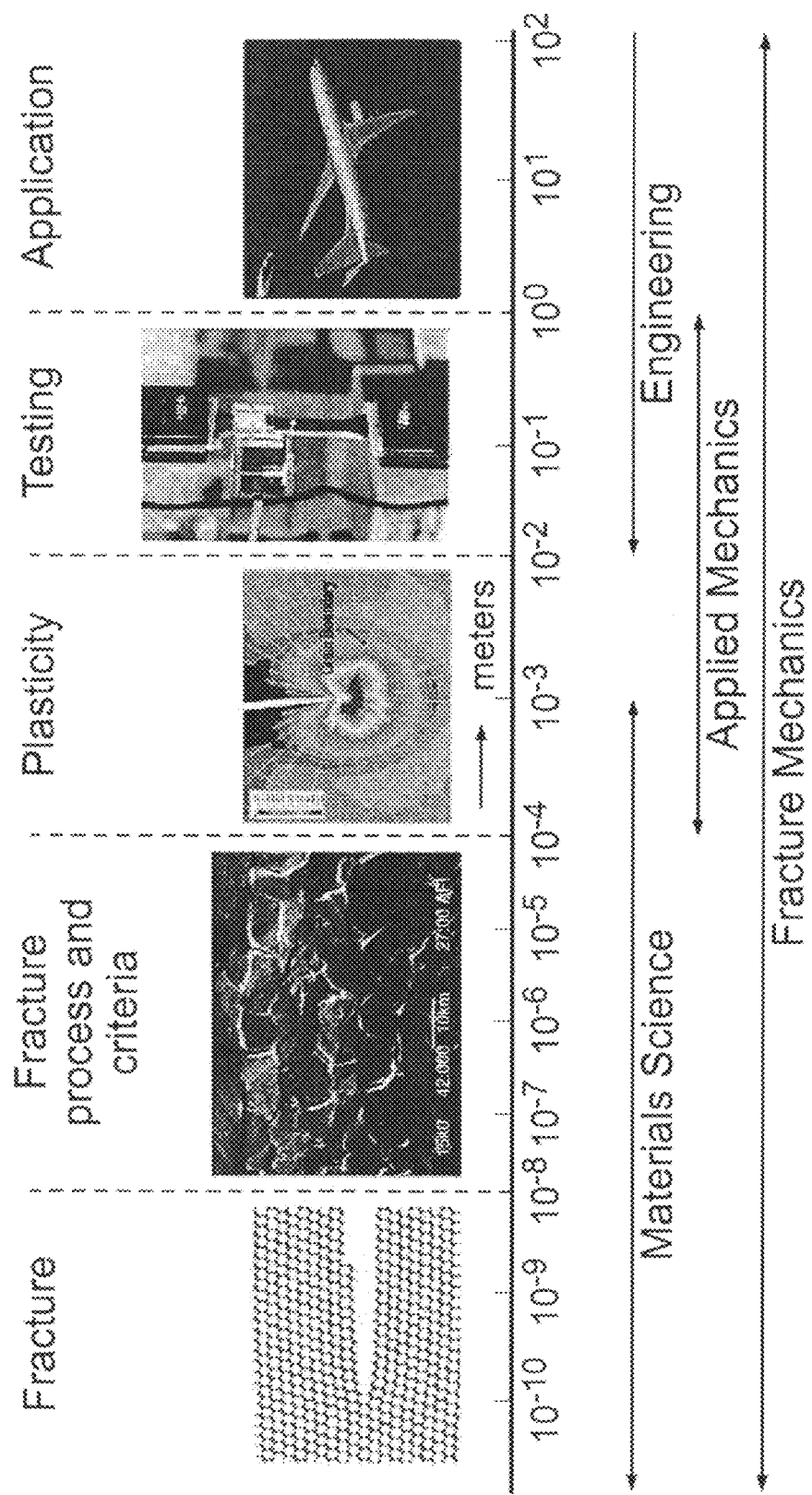
FIG. 1 is an illustration of the broad field of fracture mechanics.
Figure 2:
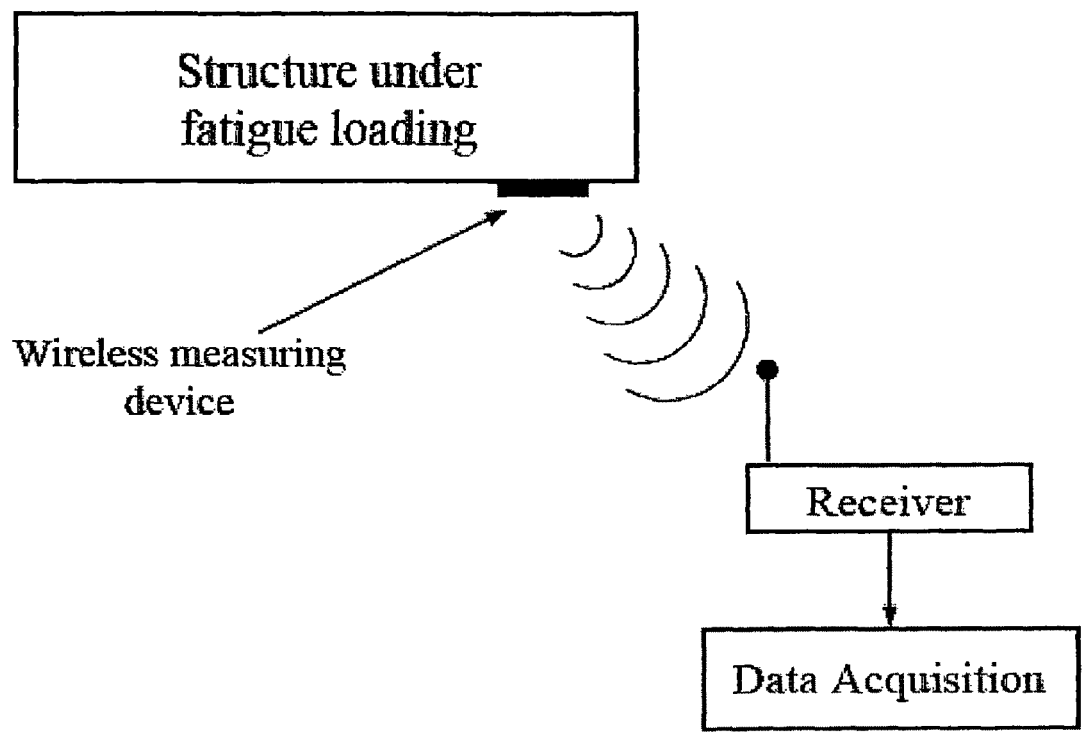
FIG. 2 is a block illustration of an embodiment of the present invention.
Figure 3A:
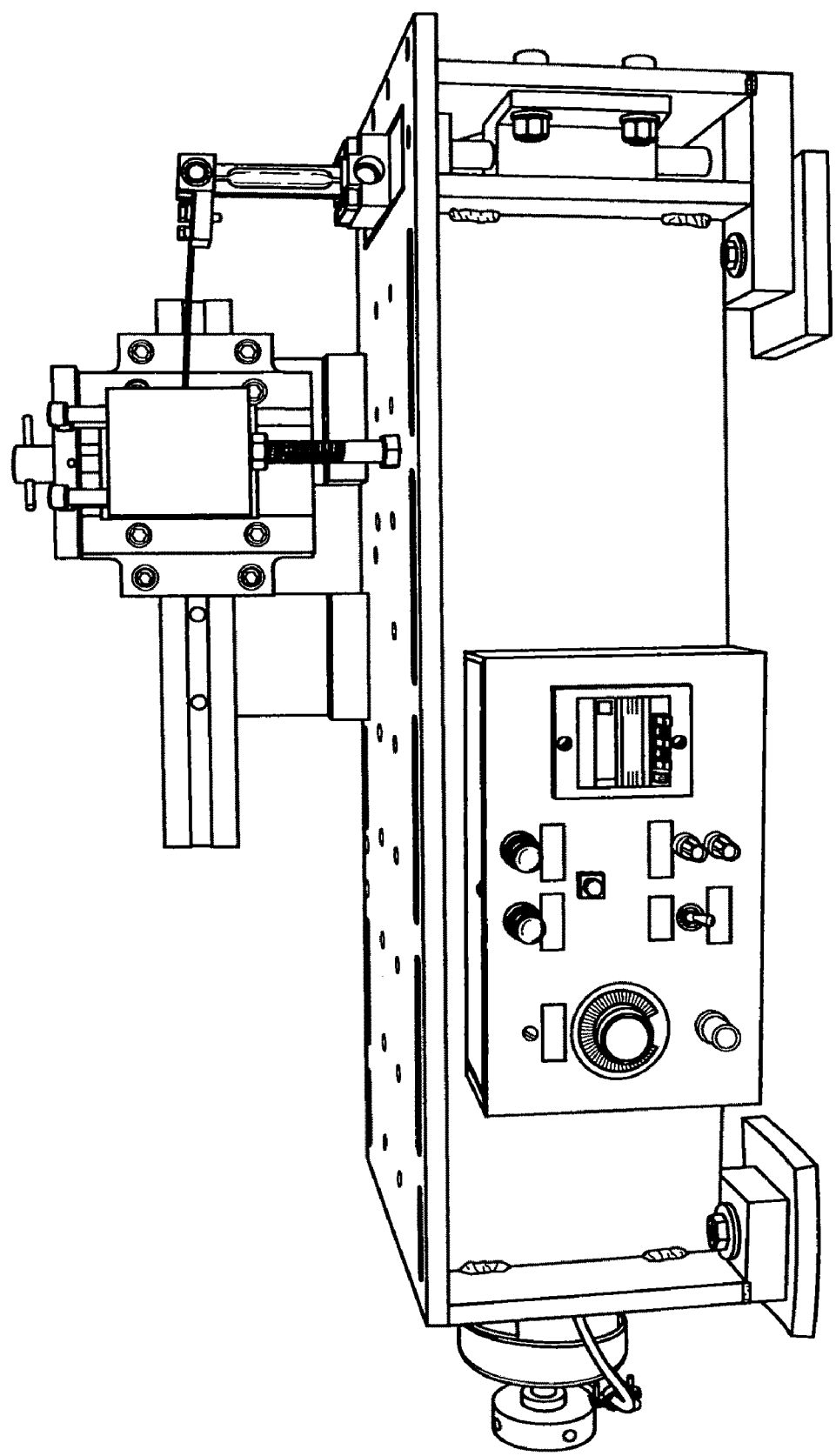
FIG. 3A is a photograph depicting an experimental apparatus for bending fatigue testing.

An extensive experimental program has been performed that involves testing pertinent types of materials of interest. These materials are used in systems that experience bending fatigue, torsion fatigue, tension/compression, as well as combined mode. A fatigue testing apparatus was used to apply cyclic bending and torsion load. The specimens used were fabricated from Aluminum and Stainless Steel. A full field surface temperature was monitored by means of an infrared camera. FIG. 3A shows the test platform used for bending fatigue testing.

Figure 3B:
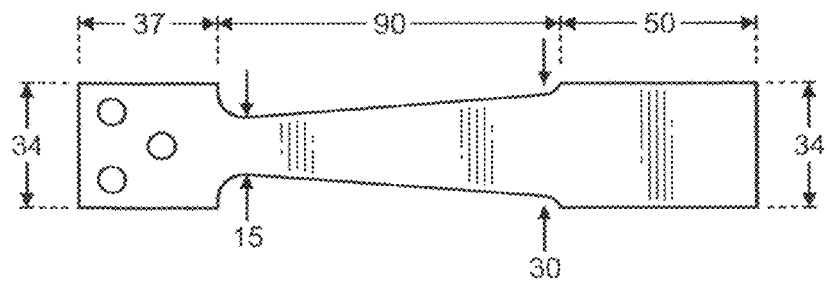
FIG. 3B is an illustration of a specimen used in bending fatigue testing.
Figure 3C:
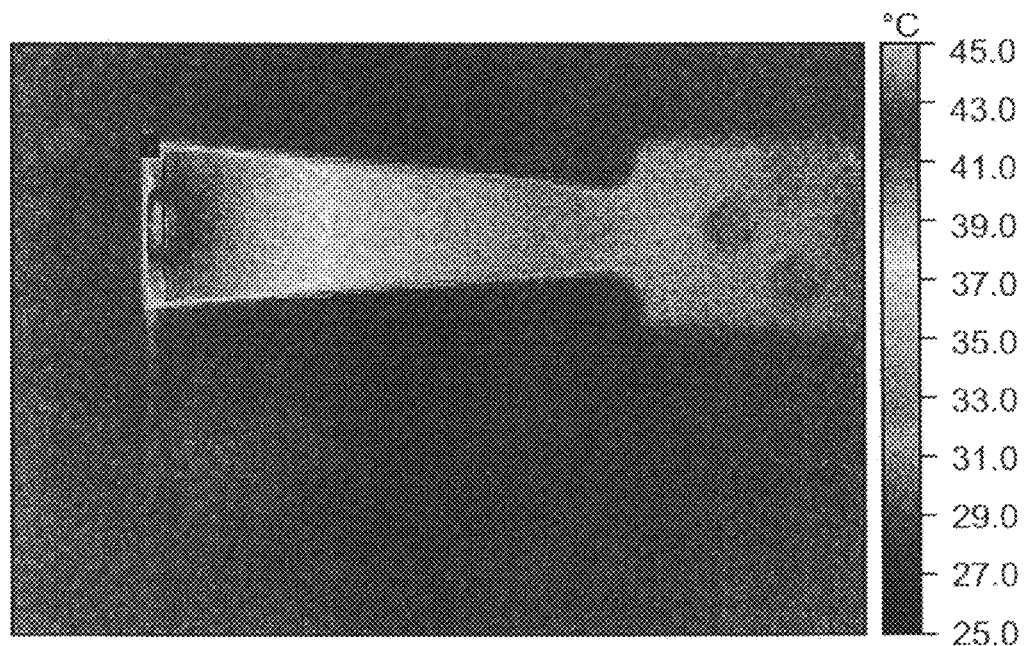
FIG. 3C is a thermal image of the specimen of FIG. 3B during bending fatigue testing.

The fatigue testing apparatus used is a compact bench mounted unit with a variable speed motor, variable throw crank connected to the reciprocating platen, a failure cut off circuit in a control box, and a cycle counter. An available option is a torsion and axial tester. FIG. 3A shows a photograph of the experimental setup used in this study to applying cyclic bending load. Fatigue tests were run until specimen complete separation. The materials used in the experiments were Aluminum (Al) and Stainless Steel (SS) plate. The specimens were fabricated to the configuration shown in FIG. 5 3B. Full field surface temperature was monitored by means of an infrared camera MIKRON M7500 with temperature range between 0° C. to 500° C., resolution of 320×240 pixel, accuracy of ±2% of reading, sensitivity/NETD of 0.08° C. at 30° C., and image update rate of 7.5 Hz. A typical thermographic image for an aluminum sample is shown in FIG. 3C. The specimens were covered with black paint to increase the emissivity of the specimen surface.

Figure 4A:
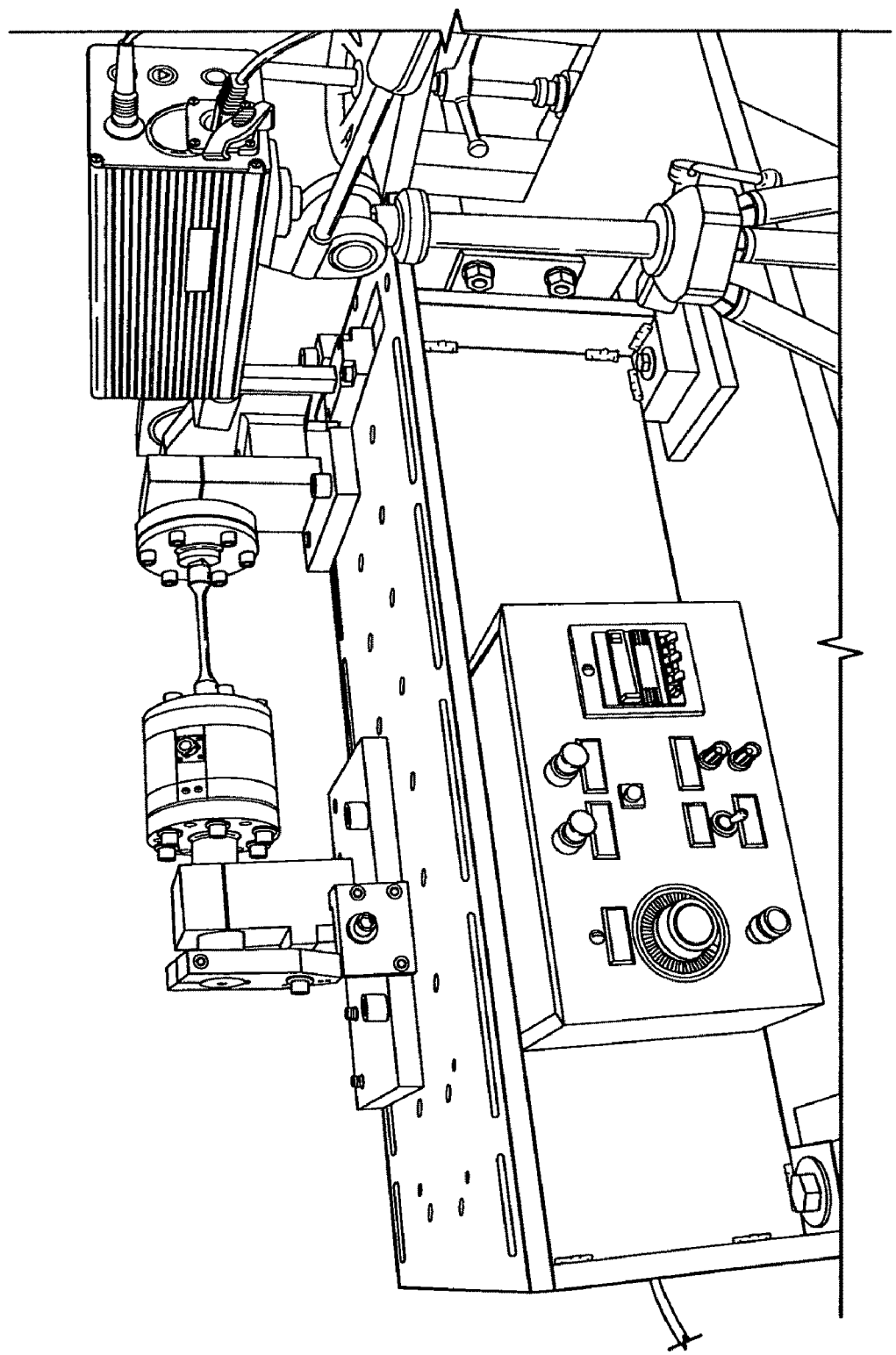
FIG. 4A is a photograph depicting an experimental apparatus for torsion fatigue testing.
Figure 4B:
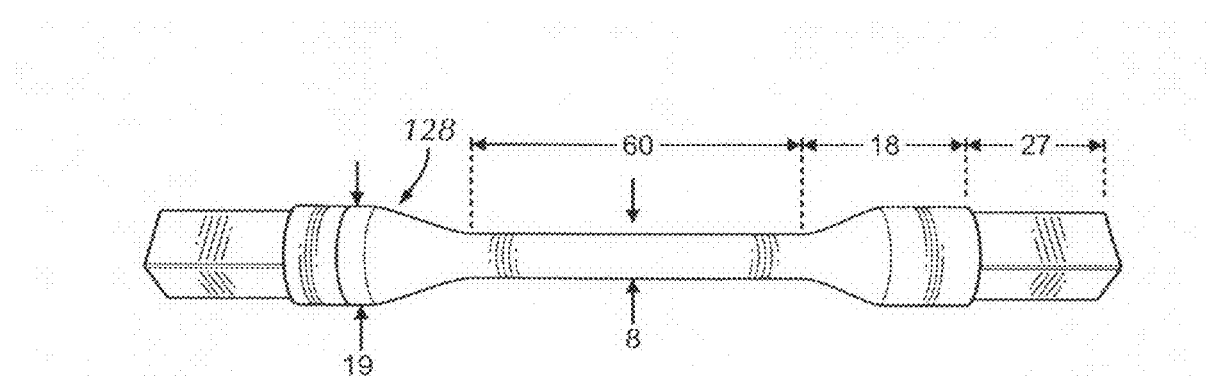
FIG. 4B is an illustration of a specimen used in torsion fatigue testing.
Figure 4C:
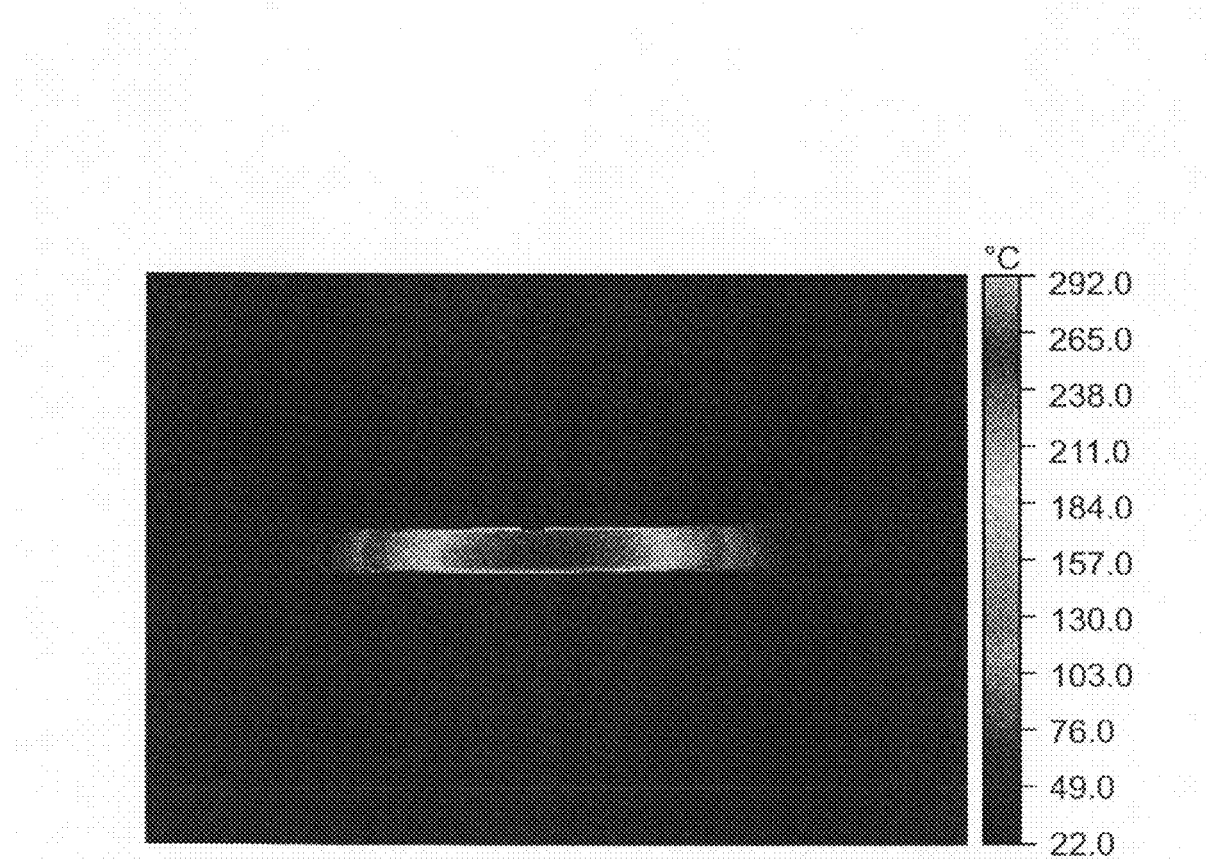
FIG. 4C is a thermal image of the specimen of FIG. 4B during torsion fatigue testing.

Torsion Fatigue. FIG. 4A shows a photograph of the experimental setup used for torsion fatigue. A series of laboratory tests was performed at a constant frequency to demonstrate the proof of concept. Fatigue tests were run until specimen complete separation, i.e. until failure occurred. The materials used in the experiments were Aluminum and Stainless Steel. The specimens were fabricated as shown in FIG. 4B and a typical temperature field after subjecting a specimen to torsion test is shown in FIG. 4C.

Figure 5:
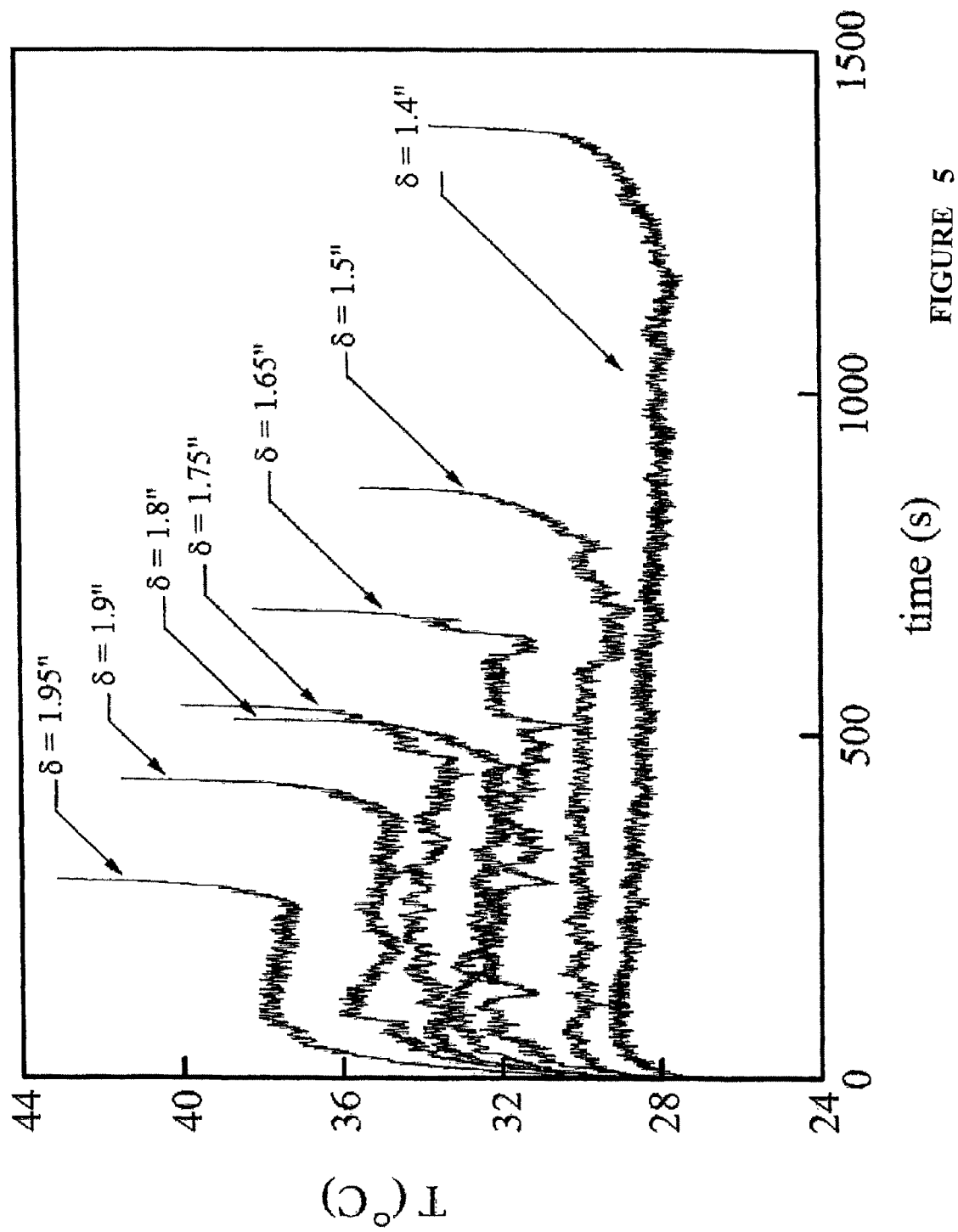
FIG. 5 is a temperature versus time plot for a series of bending fatigue tests.

The results of a series of bending fatigue tests are shown in FIG. 5. The persistent trend in all of these tests is the rapid initial rise in temperature at the beginning of the experiment followed by a period where the temperature tends to stabilize before it experiences a "temperature spike" just before the onset of failure.

Figure 6:
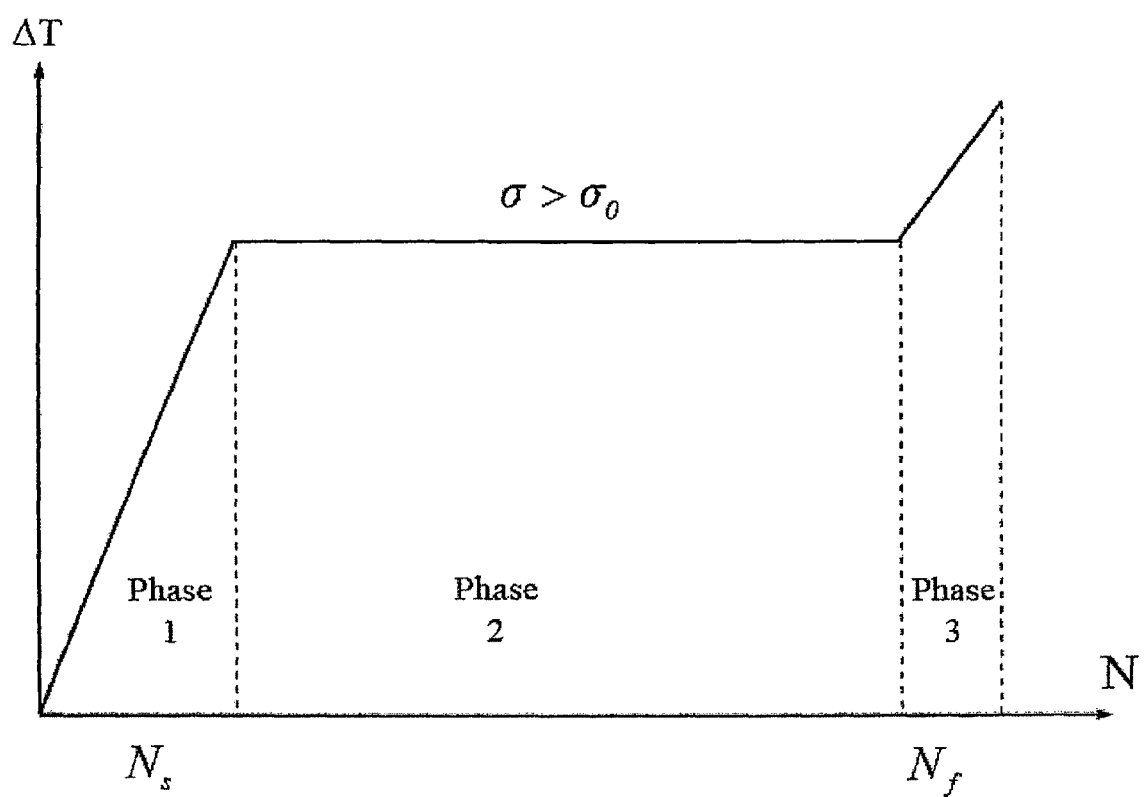
FIG. 6 is an illustrative plot of three phases of thermal behavior of a metal specimen undergoing fatigue.

This empirical analysis revealed that a material undergoing a fatigue test is subjected to an increase of the surface temperature, such that the higher the applied stress amplitude the higher the temperature increases. We have established that (FIG. 5) with the stress above the fatigue limit $\sigma_0$, the thermal variation increases during the first phase of the test (Phase 1), then remains almost constant until shortly before the failure (Phase 2) and finally shows a further increase immediately prior to failure (Phase 3). These three distinct phases are illustrated in FIG. 6.

Figure 7:
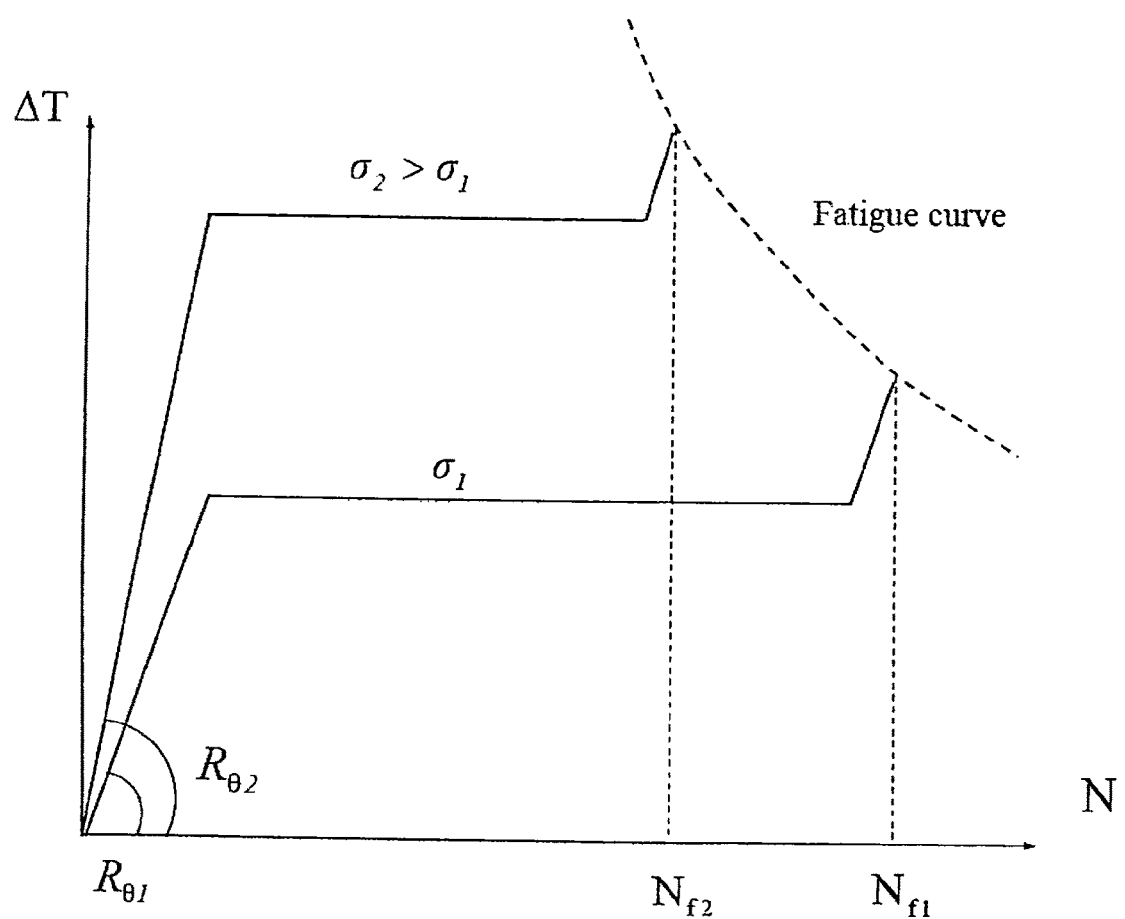
FIG. 7 is an illustrative plot showing the three phases of thermal behavior at two different stress levels.

The first phase of the temperature increase is limited to a very low number of cycles compared to the number subsequently required to reach failure (in general, in order of 10% of the entire lifespan of the specimen for loads not close to the yield stress). The second phase, of "stabilized temperature", varies considerably. For applied loads close to the yield stress this phase is extremely limited, while for loads only slightly above the fatigue limit ($\sigma_0$), it extends over almost the whole lifespan of the specimen. For loads greater than the fatigue limit, the rate of temperature increase with the number of cycles in phase 1 and the stabilization temperature in phase 2, are higher the greater the load with respect to the fatigue limit. This phenomenon is schematically shown in FIG. 7. In the third phase—the phase where failure occurs—the temperature increases rapidly for comparatively a very small number of cycles.

Based on this observation, we have developed a fatigue failure criterion based on the rate of change of temperature in the Phase 1 of the fatigue life curve. For a given set of materials parameters and the initial slope of the temperature-cycle curve, we can readily predict remaining fatigue life.

Thermal Analysis. A thermal analysis was carried out to predict the temperature of the specimen under the fatigue bending load. A two-dimensional heat conduction model was developed to analyze the problem. The present model is restricted to an isotropic bar with constant thermal conductivity. It was analytically treated using the integral transform technique [14]. The solution of the temperature distribution inside the bar is found to be as:

$$T(x, y, t) = \frac{4f\alpha\Delta w}{ak} \quad (1)$$

$$\sum_{m=1}^{\infty}\sum_{n=1}^{\infty} \frac{1}{\alpha\lambda_{mn}^2}\left[1 - e^{-\alpha\lambda_{mn}^2 t}\right]\cdot\left[(v_n^2 + H^2)\left(b + \frac{H}{v_n^2 + H^2}\right) + H\right]^{-1} \cdot$$

$$\sin\beta_m x \cdot (v_n \cdot \cos v_n y + H \cdot \sin v_n y)$$

$$\int_{x'=0}^{a}\int_{y'=0}^{b} \sin\beta_m x \cdot (v_n \cdot \cos v_n y + H \cdot \sin v_n y) \cdot dx'\,dy'$$

where T(x, y, t) is the temperature at point (x, y) and time t.

A more detailed description of the thermal analysis follows. We modeled the fluctuating beam with a finite rectangle $0 \leq x \leq a$, $0 \leq y \leq b$ initially at room temperature, $\theta_0$. For time $0<t$ heat is generated within the solid beam at a rate g(x, y, t), while the boundary conditions are shown in the model below.

(2)

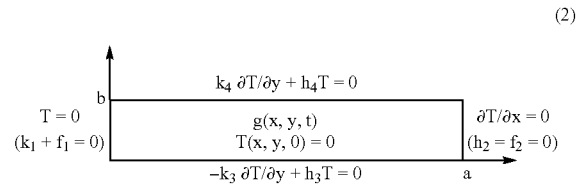

The governing equation, boundary and initial conditions for this problem are as follow:

$$\frac{\partial^2 T}{\partial x^2} + \frac{\partial^2 T}{\partial y^2} + \frac{g(x, y, t)}{k} = \frac{1}{\alpha}\frac{\partial T}{\partial t} \quad 0 \leq x \leq a, 0 \leq y \leq b, 0 < t \quad (3)$$

$$T(0, y, t) = 0, T_x(a, y, t) = 0 \quad (4)$$

$$-kT_y(x, 0, t) + h_4 T = 0, kT_y(x, b, t) + h_4 T = 0 \quad (5)$$

$$T(x, y, 0) = 0 \quad (6)$$

where $T = \theta - \theta_0$ is the temperature difference at each point and surrounding temperature. The solution of the present problem is given by [14] as follow:

$$T(x, y, t) = \sum_{m=1}^{\infty}\sum_{n=1}^{\infty} e^{-\alpha(\beta_m^2 + v_n^2)t} \cdot K(\beta_m, x) \cdot K(v_n, y) \quad (7)$$

$$\int_{t'=0}^{t} e^{\alpha(\beta_m^2 + v_n^2)t'} \cdot A(\beta_m, v_n, t') \cdot dt'$$

where $$A(\beta_m, v_n, t') =$$

$$\frac{\alpha}{k}\int_{x'=0}^{a}\int_{y'=0}^{b} K(\beta_m, x') \cdot K(v_n, y') \cdot g(x', y', t') \cdot dx'\,dy';$$

$K(\beta_m, \chi)$ and $\beta_m$ are kernel and eigenvalues along x coordinate; and, $K(v_n, y)$ and $v_n$ are the kernel and eigenvalues in y direction.

If the heat generation term, g(x, y, t), is only a function of space variable, i.e. g(x, y, t)=w(x, y) one can reduce Eq. (7) to the following:

$$A(\beta_m, v_n) = \frac{\alpha}{k} \int_{x'=0}^{a} \int_{y'=0}^{b} K(\beta_m, x') \cdot K(v_n, y') \cdot w(x', y') \cdot dx' dy' \quad (8)$$

$$T(x, y, t) = \sum_{m=1}^{\infty} \sum_{n=1}^{\infty} e^{-\alpha(\beta_m^2 + v_n^2)t} \cdot \quad (9)$$

$$K(\beta_m, x) \cdot K(v_n, y) \cdot A(\beta_m, v_n) \int_{t'=0}^{t} e^{\alpha(\beta_m^2 + v_n^2)t'} dt'$$

$$T(x, y, t) = \frac{4\alpha}{ak} \sum_{m=1}^{\infty} \sum_{n=1}^{\infty} \frac{1}{\alpha \lambda_{mn}^2} [1 - e^{-\alpha \lambda_{mn}^2 t}] \cdot \quad (10)$$

$$\left[ (v_n^2 + H^2) \left( b + \frac{H}{v_n^2 + H^2} \right) + H \right]^{-1} \cdot \sin\beta_m$$

$$x \cdot (v_n \cdot \cos v_n y + H \cdot \sin v_n y) \int_{x'=0}^{a} \int_{y'=0}^{b} \sin\beta_m x' \cdot$$

$$(v_n \cdot \cos v_n y' + H \cdot \sin v_n y') \cdot w(x', y') \cdot dx' dy'$$

where $$\lambda_{mn}^2 = \beta_m^2 + v_n^2 \quad (11)$$

$$H = \frac{h_4}{k_4} = \frac{h_{air}}{k_{metal}} \quad (12)$$

Therefore, the final solution could be found from:

$$\theta(x,y,t) = T(x,y,t) + \theta_0 \quad (13)$$

The heat generation term is assumed to be constant with time and varies only with spatial coordinate. The heat generation term inside the solid is associated with plastic deformation and can be calculated from the hysteresis loop. The dissipation energy during fatigue manifests itself as heat and causes an increase of the mean temperature. The dissipated energy density is equivalent to a constant heat source distributed in the specimen. Because the elastic stress does not contribute to the increase in the mean temperature, the elastic-stress field in the specimen could be neglected. The heat generation is mainly due to the inelastic (plastic) deformation.

It is to be noted that the room temperature is assumed to be constant and does not vary with space and time. Also, the convective heat transfer coefficient, $h_4 = h_3$, over the fluctuating beam is considered to be constant. It should be mentioned that one expects that the free end of the beam where the vertical displacement is greater than the clamped end, naturally experiences greater heat convection. However, it is a good approximation for the fixed end of the beam where the air over the surface is stationary and heat transfer is due to natural convection. The radiation heat transfer from the surface has been neglected. The heat generation term inside the solid is associated with the plastic deformation and is assumed to be constant during fatigue life as shown experimentally by Marrow [15]. The heat generation is mainly due to the inelastic deformation. In mathematically analyzing the hysteresis loops, it is best to discard the elastic strain and deal solely with the plastic strain. In this analysis, the heat generation term was calculated using the expression derived for plastic strain energy per cycle $\Delta w$, derived by Marrow [15]:

$$\Delta w = \frac{4\varepsilon'_f \left( \frac{1-n'}{1+n'} \right)}{(\sigma'_f)^{1/n'}} \sigma_a^{(1+n')/n'} \quad (14)$$

where $\sigma_a$ is the stress amplitude, n' is the cyclic strain hardening exponent, $\varepsilon'_f$ and $\sigma'_f$ are cyclic ductility and strength of the material, respectively. The stress amplitude was found from the following linear elasticity relation:

$$\sigma_a = M \frac{y}{I} \quad (15)$$

where M is the momentum and I is the second moment of inertia. Specimens for use in cantilever-beam loading are fabricated with tapered diameters proportioned to produce nominally constant stress along the test section. However, in our analysis, we assumed that the dissipated energy is equivalent to a constant heat source uniformly distributed in the specimen. Hence, the temperature distribution inside the solid bar can be found from the following:

$$T(x, y, t) = \frac{4f\alpha\Delta w}{ak} \quad (16)$$

$$\sum_{m=1}^{\infty} \sum_{n=1}^{\infty} \frac{1}{\alpha \lambda_{mn}^2} [1 - e^{-\alpha \lambda_{mn}^2 t}] \cdot \left[ (v_n^2 + H^2) \left( b + \frac{H}{v_n^2 + H^2} \right) + H \right]^{-1} \cdot$$

$$\sin\beta_m x \cdot (v_n \cdot \cos v_n y + H \cdot \sin v_n y)$$

$$\int_{x'=0}^{a} \int_{y'=0}^{b} \sin\beta_m x \cdot (v_n \cdot \cos v_n y + H \cdot \sin v_n y) \cdot dx' dy'$$

It should be mentioned that in mathematical analysis the elastic strain was discarded and plastic strain was solely taken into account. Therefore, the simulation is generally acceptable for low-cycle fatigue tests. On the other hand, in aforementioned equation (Eq. 15) which describes bending stress, a simple linear elasticity relationship was used. This assumption was made to simplify the analytical model. In the absence of any available formulation for plastic deflection of a cantilever beam, this assumption is considered to be adequate for mathematical modeling, since the main objective of presenting the analytical thermal analysis is to better understand and cross check the experimental trends.

Figure 8:
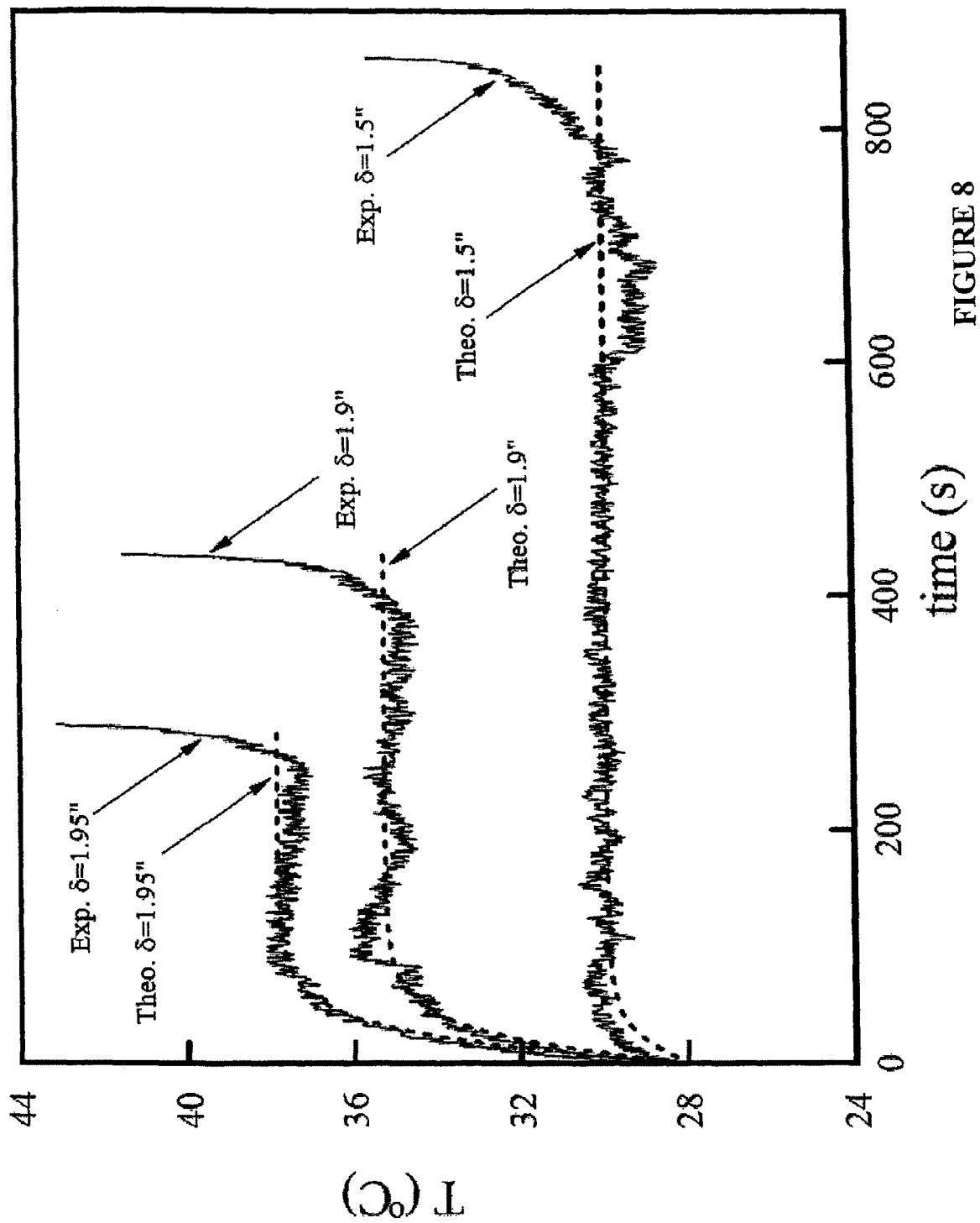
FIG. 8 is a composite plot of temperature versus time showing experimental results and analytical solutions for three different stress levels.

FIG. 8 shows the temperature distribution for Aluminum sample at 3 different stress amplitudes. It can be seen that the analytical solution accurately predicts both the initial rise in temperature and the steady state condition, well.

The surface temperature of the specimen suddenly increases just before the specimen reaches failure. This is due to occurrence of a macrocrack at the fracture point. When the macrocrack occurs, the plastic deformation at the crack tips is large. Thus, the larger the plastic deformation, the larger energy dissipation and temperature rise become.

Technology for determination of fatigue life. Based on our experimental observations, a material undergoing a fatigue test is subjected to an increase of the surface temperature such that the higher the applied stress amplitude, the greater the slope of the temperature rise. We have determined that (FIG. 7), with the stress above the fatigue limit $\sigma_0$, the thermal variation increases during the first phase of the test (Phase 1), then remains almost constant until shortly before the failure (Phase 2) and finally shows a further rapid increase immediately prior to failure, (Phase 3).

Figure 9:
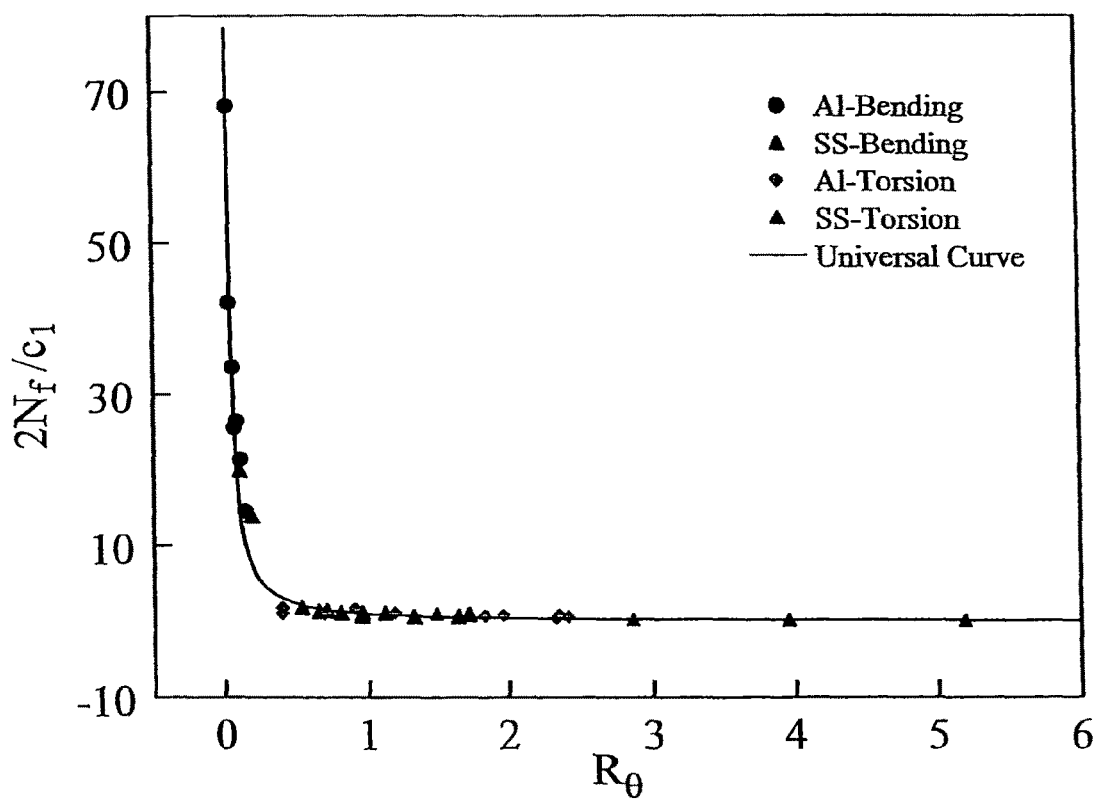
FIG. 9 is a plot showing the number of cycles to failure divided by a constant versus the slope of the temperature increase during the first phase of thermal behavior.
Figure 10:
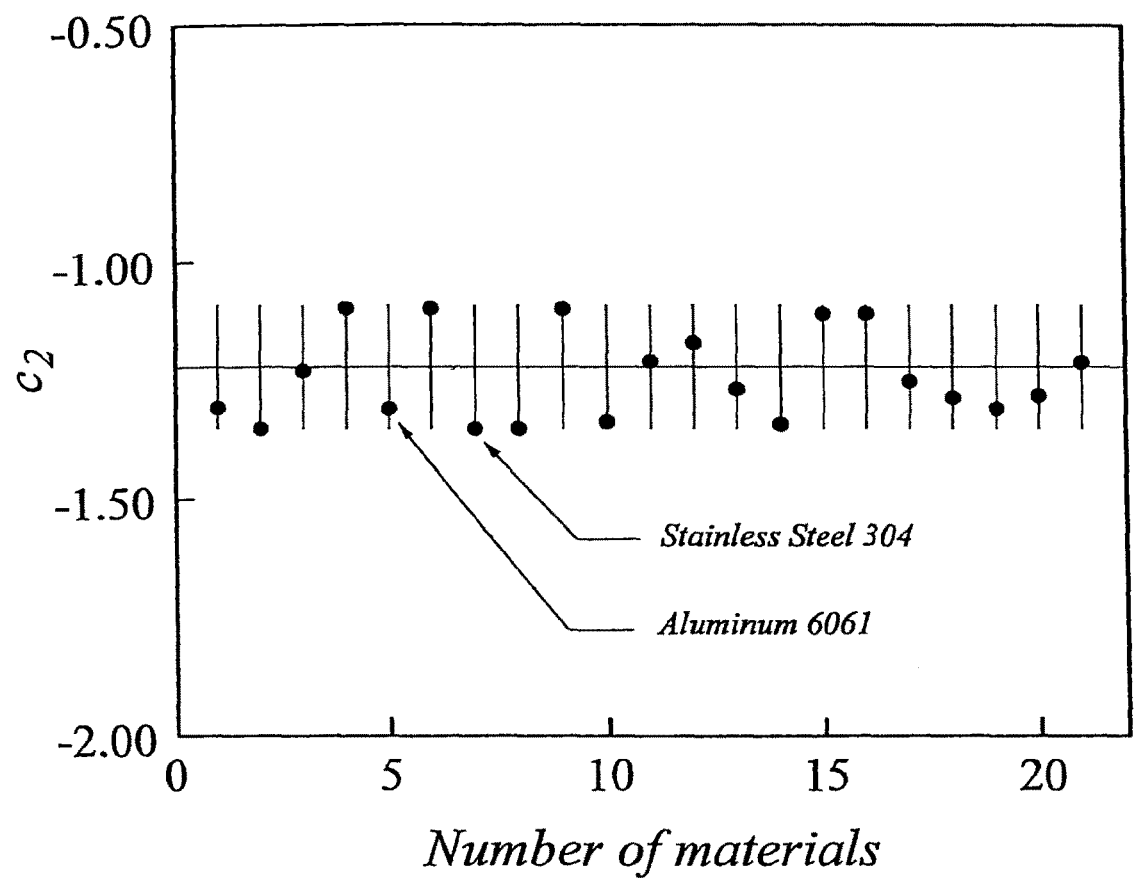
FIG. 10 is a plot of the values of a constant for a variety of types of Aluminum and Stainless Steel.

In the present invention, the slope of the temperature evolution curve during the first phase of the test (Phase 1) was effectively utilized to predict the fatigue life of the component. Both experimental tests and analytical predictions show that the number of cycles for failure, $N_f$, can be correlated to the slope of the temperature curve, $R_\theta$, as follow:

$$2N_f = c_1 R_\theta^{22} \quad (17)$$

where $c_1$ and $c_2$ are constants and dependent on the material properties and thermal boundary conditions. Experimental work of Morrow [15] showed that the value of $c_2$ for most metals is almost constant. We confirmed that the value of $c_2$ is almost identical for both several Aluminum and Stainless Steel samples (FIG. 10). Constant $c_1$, on the other hand, is almost dependent on the material properties and type of loading. Since constant $c_2$ is almost identical for both Aluminum and Steel, the results of the values of $N_f/c_1$ versus $R_\theta$ can be combined and represented in a single universal curve. FIG. 9 shows the universal fatigue-life curve as a function of slope of the temperature rise during phase one. The results of both Aluminum and Stainless Steel under bending and torsion load are plotted in this figure. Results presented in FIG. 9 are based on the experimental results and cover a life span from low to high cycle fatigue.

Once material properties and type of load are known, fatigue-life of specimen can be found at very beginning of cyclic load. The test procedure disclosed herein may be used to determine the values of $c_1$ for a wide variety of materials and load conditions. As expected, increasing the slope, results in a decrease in the fatigue life, since higher temperature slope of the temperature rise during phase one corresponds to a larger applied load and consequently lower life duration. The correlation presented in FIG. 9 is for initially intact specimens. An advantage of the method is that merely by measuring the slope of the temperature rise during phase one, we can predict the fatigue life. The sensor can be installed, in situ, and the measurements are taken while the component is in service. In contrast, other techniques require stopping the components or the machine for the purpose of inspection. Moreover, the length scale of the component/structure being tested does not present a problem. That is, the same method can be used in a micro device or extremely large structures such as windmill blades. Our experimental results cover the entire range of fatigue, i.e. both low-cycle and high-cycle.

Determination of remaining life of a machine. This invention provides a technique to predict the remaining service life of a structure already undergoing fatigue load. In the experiments conducted, we utilized specimen that were initially intact. If the material undergoing fatigue test is initially damaged or has experienced loading, its behavior under the fatigue test is different from the intact material.

Tzou [16] studied the thermal response of the solids which have existing cracks in their structures. He concluded that in companion with the degradation of elastic moduli due to microcracks, degradation of thermal conductivity may significantly increase the temperature established in the solid. Due to large volumetric strain developed in the neighborhood of a macrocrack tip, for example, the number density of microcracks dramatically increases in the strain history. The resulting degradation of thermal conductivity in the local area prevents heat from dissipating into the surrounding media and a localized temperature spike is thus found. He proposed a relation between thermal conductivity (K) of the solid and the damage parameter (D) as follows:

$$\frac{K}{K_0} = 1 - \frac{16}{9}\left(\frac{1-v^2}{1-2v}\right)C_d = 1 - D \quad (18)$$

where $C_d$ is the microcrack density parameter, v the Poisson's ratio, and ($K_o$) is the intact value of thermal conductivity.

Considering the governing equation of heat conduction, Eq. (3), the temperature rise (or slope of the temperature) can change by changing the value thermal conductivity due to microcrack initiation and propagation. Therefore, with the methodology reported in our invention, i.e. by measuring the slope of the temperature curve, during phase one, we are able to determine the integrity of the material and consequently estimate the remaining fatigue life of an existing structure or component.

Accelerated testing technique. This invention provides a rapid and effective technique for conducting accelerated testing for evaluation of degradation in materials. Development of an accelerated testing methodology has long been a major challenge in applied science and technology. It refers to the development of an enabling technology for predicting the long-time range behavior of a structure or a component based on tests that are conducted over a short length of time. Traditional life data analysis involves analyzing times-to-failure data (of a product, system or component) obtained under normal operating conditions in order to quantify the life characteristics of a specimen, a system or a component. In many situations, for many reasons, such life data analysis (or times-to-failure data) is very difficult—if not impossible—to obtain. Two methods are available: usage rate acceleration and overstress acceleration. These methods have been used to obtain time-to-failure data at an accelerated pace. For products that do not operate continuously, one can accelerate the time it takes to induce failures by continuously testing these products. This is called usage rate acceleration. For products for which usage rate acceleration is impractical, one can apply stress(es) at levels which exceed the levels that a product will encounter under normal use conditions and use the times-to-failure data obtained in this manner to extrapolate to use conditions. This is called overstress acceleration.

The method reported in our invention would be applicable to any mechanical machine application that has cyclic fatigue crack initiation and crack propagation potential to determine useful life. Since over 90% of mechanical failures are due to fatigue damage, the present invention will be useful in many industries which employ dynamically loaded mechanical systems. Of particular significance are applications in the aircraft industries, military, marine, automotive, sensitive components such as pressure vessels, and bridges/structural applications where fatigue failure is a major concern.

Proposed Method for Determining the Fatigue Life

Based on the experimental observation, surface temperature of a metallic object undergoing a fatigue test experiences three distinct phases: an abrupt rise in temperature (phase one), followed by a steady state trend (phase two), and finally a sharp increase in temperature immediately prior to failure (phase three).

Using the thermal model discussed above, equation (19) gives us transient temperature distribution inside the bar as follow:

$$T(x,y,t) = \frac{4f\alpha\overline{\Delta w}}{ak}\sum_{m=1}^{\infty}\sum_{n=1}^{\infty}\frac{1}{\alpha\lambda_{mn}^2}[1-e^{-\alpha\lambda_{mn}^2 t}] \cdot \quad (19)$$

$$\left[(v_n^2+H^2)\left(b+\frac{H}{v_n^2+H^2}\right)+H\right]^{-1} \cdot$$

$$\sin\beta_m x \cdot (v_n \cdot \cos v_n y + H \cdot \sin v_n y)\int_{x'=0}^{a}\int_{y'=0}^{b}\sin$$

$$\beta_m x \cdot (v_n \cdot \cos v_n y + H \cdot \sin v_n y) \cdot dx'\, dy'$$

By setting y=b or y=0 we can find the temperature variation over the beam surface. Making the time derivative of Eq. (19), gives the expression for the rate of temperature rise over the top surface of the beam. On the other hand, we can find a relationship between the heat generation term in the above equation, w(x, y), and the number of cycles for fatigue failure, as proposed by Marrow [15]:

$$\overline{\Delta w} = 4\varepsilon'_f \sigma'_f \left(\frac{c-b}{c+b}\right)(2N_f)^{b+c} \quad (20)$$

In this equation all the parameters except $\overline{\Delta w}$ and $N_f$ are the properties of material. Substituting Eq. (20) into the equation obtained by making the time derivative of Eq. (19) gives us a relationship between the rate of temperature rise during phase one and the number of cycles for fatigue failure, $N_f$.

$$\left.\frac{\partial T}{\partial t}\right|_{t=0, y=b} = f(N_f) \quad (21)$$

$$\left.\frac{\partial T}{\partial t}\right|_{t=0} = R_\theta = 4\varepsilon'_f \sigma'_f \left(\frac{c-b}{c+b}\right)(2N_f)^{b+c} \cdot \Psi \quad (22)$$

where $$\Psi = \frac{4f\alpha}{ak} \sum_{m=1}^{\infty} \sum_{n=1}^{\infty} \left[(v_n^2 + H^2)\left(b + \frac{H}{v_n^2 + H^2}\right) + H\right]^{-1} \cdot \quad (23)$$

$$\sin\beta_m x \cdot (v_n \cdot \cos v_n y + H \cdot \sin v_n y) \int_{x'=0}^{a} \int_{y'=0}^{b} \sin\beta_m x' \cdot$$

$$(v_n \cdot \cos v_n y + H \cdot \sin v_n y) \cdot dx' \, dy' = const.$$

Eventually, the number of cycles for fatigue failure can be expressed as a function of slope of the curve:

$$2N_f = \left[\frac{R_\theta}{4\varepsilon'_f \sigma'_f \cdot \left(\frac{c-b}{c+b}\right) \cdot \Psi}\right]^{\frac{1}{b+c}} = c_1 R_\theta^{c_2} \quad (24)$$

Figure 11:
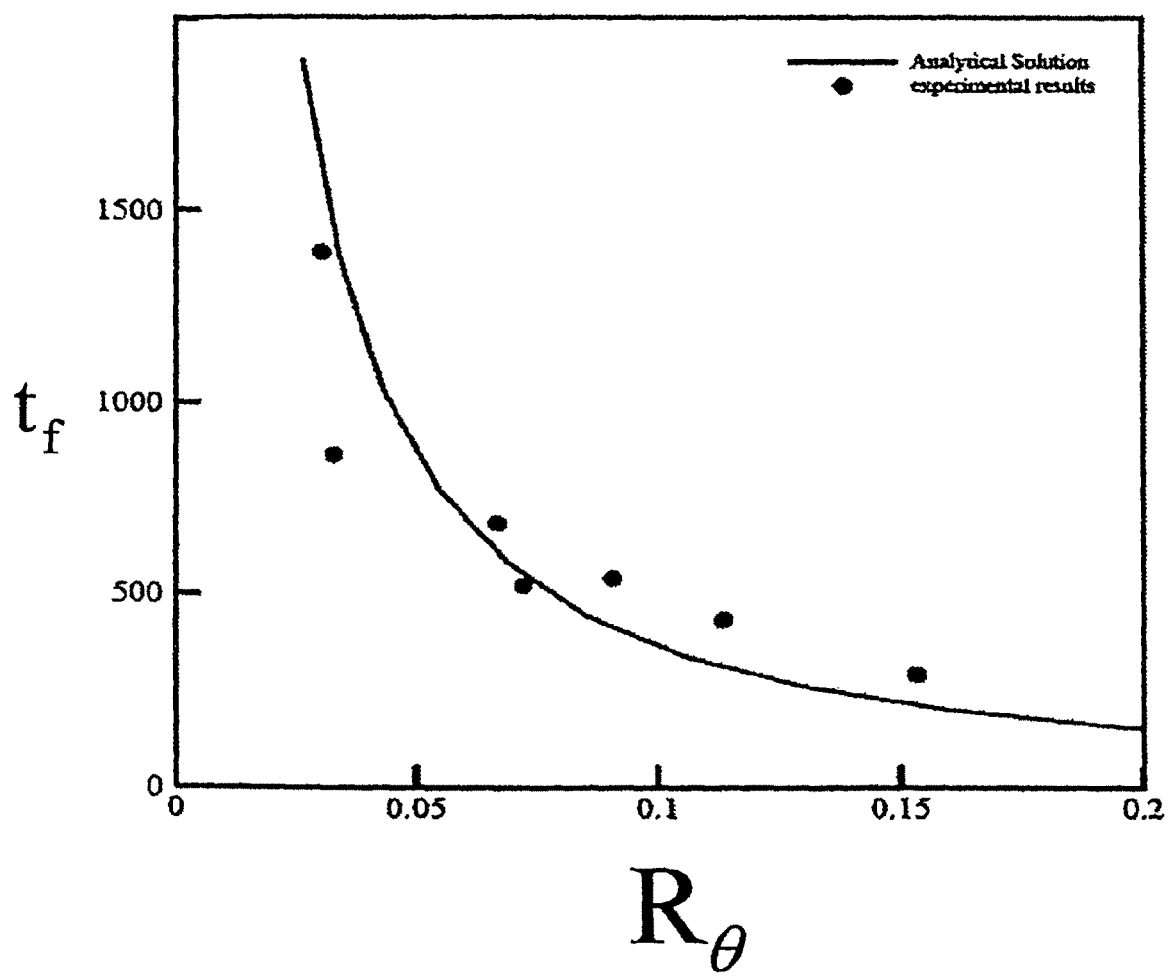
FIG. 11 is a plot of fatigue failure prediction as a function of the slope of the temperature increase during the first phase of thermal behavior for an Aluminum specimen.
Figure 12:
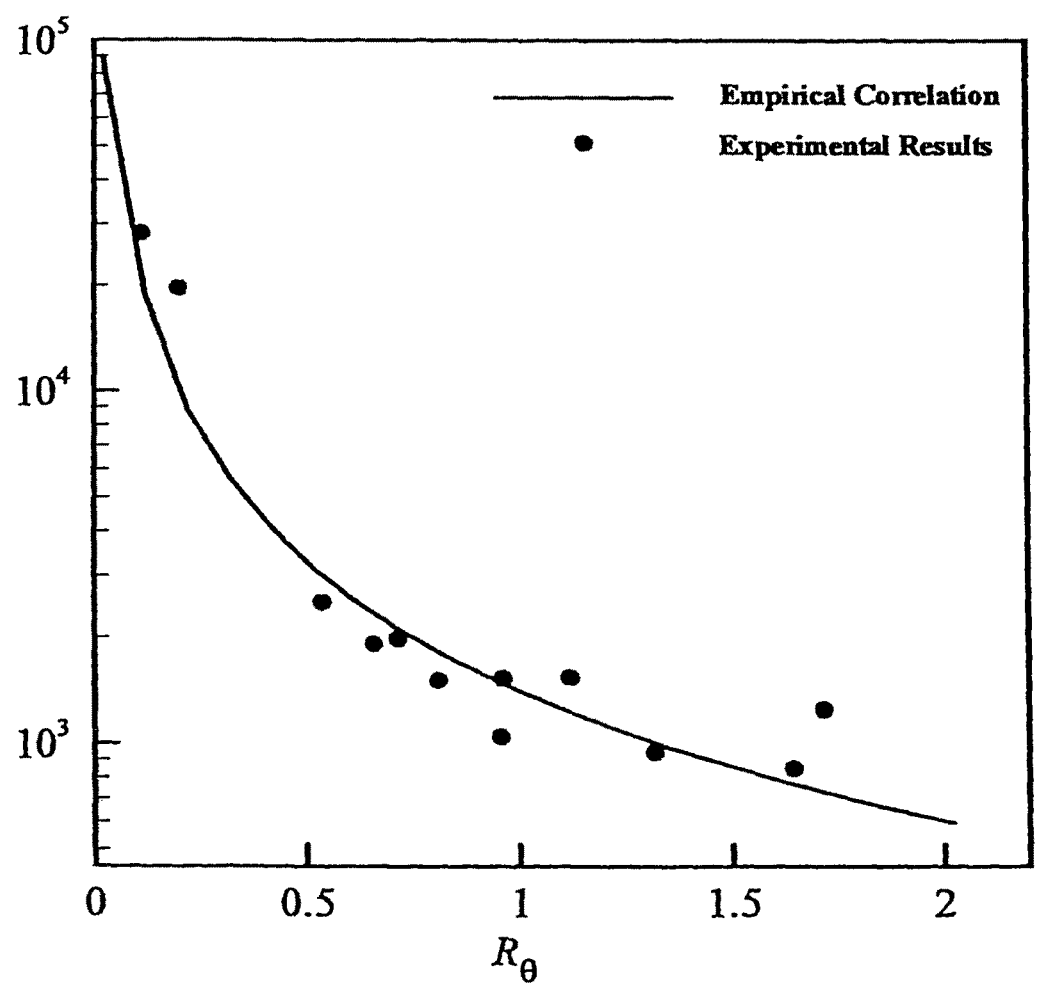
FIG. 12 is a plot of fatigue failure prediction as a function of the slope of the temperature increase during the first phase of thermal behavior for a Stainless Steel specimen.

In order to check the accuracy of our thermal analysis, we compared the experimental results and the predicted number of cycles for bending fatigue load. FIG. 11 shows the results for the Aluminum specimen. The ordinate of FIG. 11 shows the time to complete failure (fracture of specimen into two parts) of the specimen, $t_f$, and the abscissa shows the slope of the temperature curve at the beginning of the test, $R_\theta$. FIG. 12 shows the experimental results of the Stainless Steel specimen along with the empirical correlation. Results presented in this figure cover a range of data from low-cycle to high-cycle fatigue.

Figure 13:
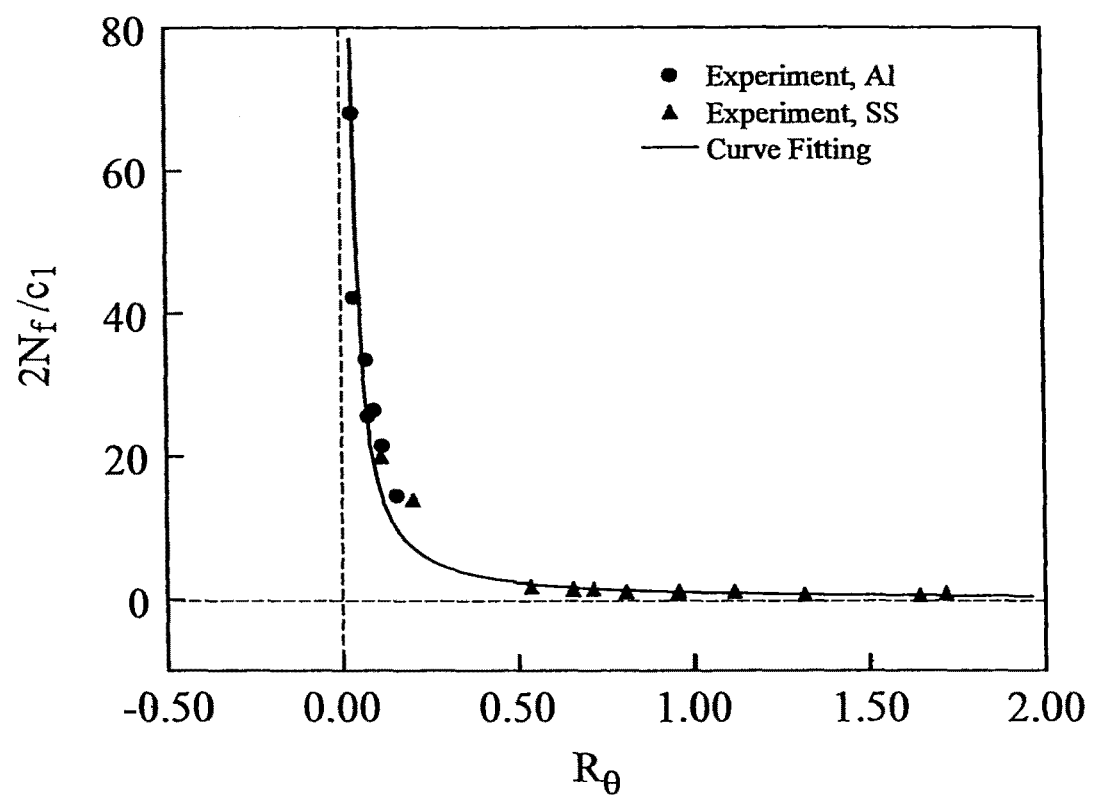
FIG. 13 is a composite plot showing bending results for both Aluminum and Stainless Steel specimens.
Figure 14:
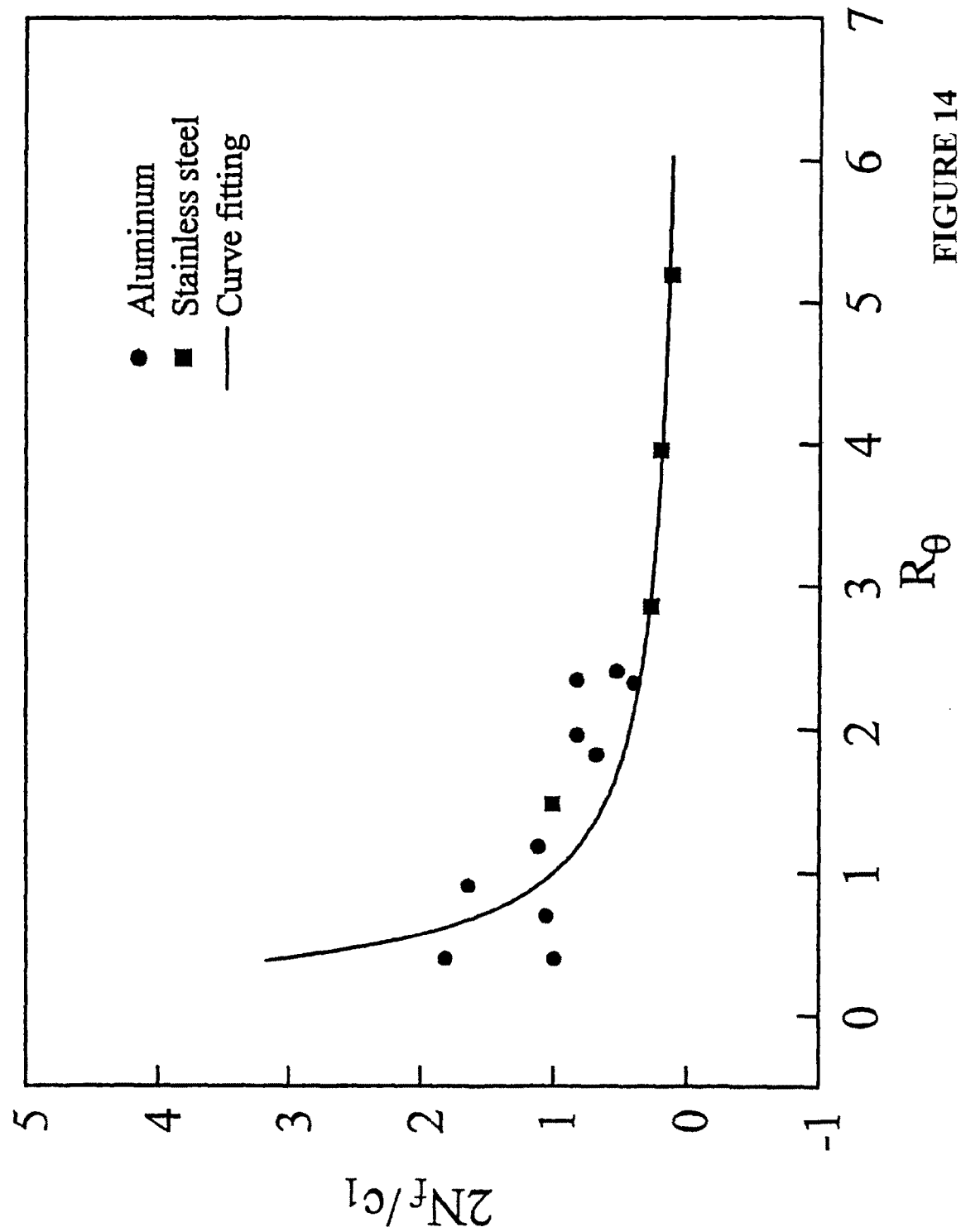
FIG. 14 is a composite plot showing torsion results for both Aluminum and Stainless Steel specimens.

Constants $c_1$ and $c_2$ in Eq. (24) are dependent on the material properties and thermal boundary conditions. Experimental work of Morrow [15] showed that the value of (b+c) for most metals is almost constant. Subsequently, $c_2$ is identical for both Aluminum and Steel, as seen by the results shown in FIG. 10. Based on this observation, FIG. 13 shows the experimental results of bending load for Aluminum and Stainless Steel specimens along with a unique curve which best fits the experimental data points. It is to be noted that for both materials the value of $c_2$ used to get a good curve fit is the same. The same procedure was used to represent the experimental results of torsion for each Aluminum and Stainless Steel with an empirical correlation. Again, the exponent $c_2 = -1.22$ is identical for both Aluminum and Stainless Steel under torsion fatigue load. FIG. 14 shows the experimental results of torsion along with the empirical curve fitted to the data.

The value of $c_1$ for Aluminum in bending and torsion is 204 and 8120 respectively. The $c_1$ values determined for Stainless Steel for bending and torsion are 14,102 and 183,830, respectively. Values of $c_1$ can be determined for other materials and other loading conditions using the test procedure and analytical relationships set out above.

The value of $c_1$ may be estimated using the analytical methods described above. In particular, equation 24 shows that $$c_1 = \left[\frac{1}{4\varepsilon'_f \sigma'_f \cdot \left(\frac{c-b}{c+b}\right) \cdot \Psi}\right] \quad (25)$$

where all parameters are as defined above.

If the material properties and thermal boundary conditions are known, equation 25 may be solved for $c_1$. When this was done for an Aluminum sample under bending load, the results were consistent with the empirically derived values. Similar calculations could be performed for other materials and loading conditions.

The $c_1$ value is derived empirically by plotting the data points as shown in FIGS. 13 and 14. Data points are plotted using the value of $c_2 = -1.22$, and the value of $c_1$ is varied in equation of 17 until the best curve fit is obtained. The values for $c_1$ recited above were determined in this manner. The same method could be performed using other materials and different load conditions. Using this method, the experimental data points for each material and loading type are plotted in diagram, for example, with the y-axis representing the number of cycles to failure ($N_f$) and the x-axis representing the slope ($R_\theta$) of the temperature increase during phase one. A curve fit process is then used to fix the value of $c_1$ using equation 17.

The value for $c_2$ used in this method can be varied, but it is preferred to begin with a value of approximately −1.22, which is the empirically derived value found for Aluminum and Stainless Steel subject to either bending or torsion loading. Because Aluminum and Stainless Steel have significantly different properties in many respects, the fact that both materials resulted in the same value for the constant $c_2$ strongly suggests that other metals would have the same, or at least a very similar, value for $c_2$.

After an initial curve fit analysis is done with the value of $c_2$ set at −1.22, additional curve fits may be performed with different values for $c_2$. The range of −1.10 to −1.35 was found to encompass almost all test results for the constant $c_2$. This range, therefore, should be sufficient to perform additional curve fit analyses, in order to obtain the overall best curve fit using the empirical data plotted as described above. Through use of this method, the values of the constants $c_1$ and $c_2$ may be accurately determined for any material and any cyclic loading conditions. Once these constants are determined, equation 17 may be used to predict the service life. The present invention, therefore, is applicable to a broad range of materials and real-world conditions.

The value of $c_2$ remains nearly constant for most metals and loading conditions. Aluminum and Stainless Steel are quite different metals in many respects, yet the $c_2$ value for these metals is nearly constant. As FIG. 10 shows, when approximately 20 samples of different types of Aluminum and Stainless Steel were tested, the $C_2$ ranged from −1.09 to −1.35 (i.e., 0.13 above and below the −1.22 value identified above). The analytic prediction of $c_2$ described above produced estimates of $c_2$ in the range of −1.3 to −1.35, which further confirms the stable value of this constant. Based on these results, it is reasonable to use a value of $c_2$=−1.22 in the process of evaluating other metals. This greatly simplifies the process of determining the values of the constant $c_1$ for different materials and conditions.

REFERENCES

[1] D. Broek, "Elementary Engineering Fracture Mechanics", 1982, Martinus Nijhoff Publishers.
[2] G. Fargione, A. Geraci, G. La Rosa, and A. Risitano, "Rapid Determination of the Fatigue Curve by the Thermographic Method," *Int. J. Fatigue*, vol. 24, No. 1, 2002, pp. 11-19.
[3] H. Wang, L. Jiang, C. R. Brooks, and P. K. Liaw: *Metall. Mater. Trans. A*, 2000, vol. 31A, pp. 1307-1310.
[4] P. K. Liaw, H. Wang, L. Jiang, B. Yang, J. Y. Huang, R. Q. Kuo, and J. G. Huang: *Scripta Mater.*, 2000, vol. 42, pp. 389-395.
[5] R. Blotny, K. Kaleta, W. Grzebien, and W. Adamczewski: *Int. J. Fatigue*, 1986, vol. 8 (1), pp. 35-38.
[6] B. I. Sandor, D. T. Lohr, and K. C. Schmid: *Mater. Eval.*, 1987, vol. 45(4), pp. 382-395.
[7] R. Attermo and G. Ostberg: *Int. J. Fract. Mech.*, 1971, vol. 7, pp. 122-124.
[8] D. T. Lohr, N. F. Enke, and B. I. Sandor: *Dynamic Failure: Proc. 1987 Society for Experimental Mechanics (SEM) Fall Conf.*, Savannah, Ga., Oct. 25-26, 1987, SEM, Brookfield Center, Conn., pp. 139-174.
[9] T. Gross: Ph.D. Thesis: Northwestern University, Evanston, Ill., 1981.
[10] M. P. Luong: *Nucl. Eng. Design*, 1995, vol. 158, pp. 363-376.
[11] M. P. Luong: *Mech. Mater.*, 1998, vol. 28, pp. 155-163.
[12] J. A. Charles, F. J. Appl, and J. E. Francis: Trans. *ASME*, 1978, vol. 100 (4), pp. 200-203.
[13] Y. Huang, S. X. Li, S. E. Lin, and C. H. Shih: *Mater. Eval.*, 1984, vol. 42 (7), pp. 1020-1024.
[14] M. Necati Ozisik, "Boundary Value Problems of Heat Conduction", 2002, Dover Publications.
[15] J. D. Morrow, "Cyclic Plastic Strain Energy and Fatigue of Metals,", *Internal Friction, Damping, and Cyclic Plasticity, ASTM STP* 378, 1965, pp. 45-84.
[16] D. Y. Tzou, "Deformation Induced Degredation of Thermal Conductivity in Cracked Solid," *J. Composite Materials*, vol 28, 1994, pp: 886-901.

We claim:

1. A method of predicting the service life of an object subject to cyclic loading, comprising:
   a. monitoring the surface temperature of the object with a temperature sensor;
   b. determining, with a processor, the slope ($R_\theta$) of the increase in surface temperature of the object during a first phase, wherein the first phase is defined as a period of relatively rapid increase in surface temperature of the object from its initial temperature; and,
   c. predicting with a processor the service life of the object in number of cycles to failure ($2N_f$) using the equation:

$2N_f = c_1 R_\theta^{c_2}$, wherein $c_1$ and $c_2$ are constants.

2. The method of claim 1, wherein the first phase is followed by a second phase during which the surface temperature of the object is relatively stable.

3. The method of claim 1, where the constant $c_2$ has a value of approximately −1.22.

4. The method of claim 1, wherein the object is Aluminum subjected to a cyclic bending stress, and where the constant $c_2$ has a value of approximately −1.22 and the constant $c_1$ has a value of approximately 204.

5. The method of claim 1, wherein the object is Aluminum subjected to a cyclic torsion stress, and where the constant $c_2$ has a value of approximately −1.22 and the constant $c_1$ has a value of approximately 8120.

6. The method of claim 1, wherein the object is Stainless Steel subjected to a cyclic bending stress, and where the constant $c_2$ has a value of approximately −1.22 and the constant $c_1$ has a value of approximately 14,102.

7. The method of claim 1, wherein the object is Stainless Steel subjected to a cyclic torsion stress, and where the constant $c_2$ has a value of approximately −1.22 and the constant $c_1$ has a value of approximately 183,830.

8. The method of claim 1, wherein the object was formed from a metal or metal alloy, and wherein the value of $c_2$ is determined using the equation $c_2 = 1/(b+c)$, where b is the fatigue strength exponent and c is the fatigue ductility coefficient for the metal or metal alloy from which the object was formed.

9. A method of determining the value of a constant ($c_1$), comprising:
   a. plotting with a processor experimental data points for a test specimen subjected to cyclic loading where the data points include
      i. the number of cycles to failure ($2N_f$); and,
      ii. the slope ($R_\theta$) of the increase in surface temperature of the test specimen during a first phase, wherein the first phase is defined as a period of relatively rapid increase in surface temperature from its initial temperature that is followed by a second phase during which the surface temperature is relatively stable;
   b. fitting a curve with a processor to the plotted experimental data points using the equation $2N_f = c_1 R_\theta^{c_2}$, where the value of $c_2$ is estimated, and the value of $c_1$ is varied until the best curve fit is obtained, thus fixing the value of the constant $c_1$.

10. The method of claim 9, wherein value of −1.22 is used for the constant $c_2$ in the curve fit process.

11. The method of claim 9, wherein the constant $c_2$ is assigned an estimated value in the range of −1.10 to −1.35.

12. A method of determining a value for a constant ($c_2$) for a material of interest subject to a cyclic loading stress, comprising:
   a. determining the fatigue strength exponent (b) for the material of interest subject to the cyclic loading stress, with a fatigue testing apparatus;
   b. determining the fatigue ductility coefficient (c) for the material of interest subject to the cyclic loading stress, with a fatigue testing apparatus; and,
   c. calculating with a processor the constant ($c_2$) using the equation $c_2 = 1/(b+c)$.

13. A method of determining values for two constants ($c_1$ and $c_2$) for a material of interest subject to a cyclic loading stress, comprising:
   a. plotting with a processor experimental data points for a test specimen subjected to the cyclic loading stress where the data points include
      i. the number of cycles to failure ($2N_f$); and,
      ii. the slope ($R_\theta$) of the increase in surface temperature of the test specimen during a first phase, wherein the first phase is defined as a period of relatively rapid increase in surface temperature from its initial temperature that is followed by a second phase during which the surface temperature is relatively stable;

b. fitting a curve with a processor to the plotted experimental data points using the equation $2N_f = c_1 R_\theta^{c_2}$, and through performance of the following steps:

i. performing a first curve fit analysis with the value of $c_2$ being set at approximately −1.22, and the value of $c_1$ varied until the best curve fit is obtained;

ii. performing subsequent curve fit analyses, as needed, using values of $c_2$ within the range of approximately −1.10 to −1.35, and with different values of $c_1$, until an overall best curve fit is obtained, thus fixing the values of $c_1$ and $c_2$.

14. A method of determining a slope of an increasing surface temperature of a metallic test specimen, comprising:

a. obtaining a test specimen of appropriate dimensions and shape for bench testing using a device for imposing a cyclic loading stress;

b. applying a cyclic loading stress to the test specimen with a fatigue testing apparatus;

c. monitoring the surface temperature of the test specimen with a temperature sensor;

d. determining when a first phase has ended by noting with a processor when the surface temperature stops rising rapidly and becomes relatively stable; and, e. determining with a processor the slope of the rise in surface temperature over time during the first phase.

15. A method of predicting the service life of a metallic object subject to cyclic loading, comprising:

a. determining with a processor the slope of increase in surface temperature of the metallic object during a first phase of operation, wherein, i. the first phase is defined by a period of relatively rapid increase in surface temperature from its initial temperature; and, ii. the first phase is followed by a second phase during which the surface temperature remains relatively constant;

b. predicting with a processor the service life of the object based on the slope of the increase in surface temperature during the first phase of operation.

16. An apparatus for predicting the service life of a metallic object subject to cyclic loading, comprising:

a. a temperature sensing device configured to monitor the surface temperature of the metallic object;

b. a data analysis unit that receives temperature data from the temperature sensing device and computes a predicted service life of the object using the equation $2N_f = c_1 R_\theta^{c_2}$, wherein $2Nf$ is the number of cycles to failure; $R_\theta$ is the slope of the temperature change during a first phase of operation;

and $c_1$ and $c_2$ are constants, and wherein, i. the first phase of operation is defined as a period during which the surface temperature rises rapidly from its initial temperature and is followed by a second phase during which the surface temperature is relatively constant.

17. The apparatus of claim 15 wherein the temperature sensor is a wireless device that sends temperature data to a receiver located remote to the object.

18. The method of claim 1, wherein the object is metallic.

19. The method of claim 9, wherein the specimen is metallic.

20. The method of claim 12, wherein the material is metallic.

21. The method of claim 13, wherein the material is metallic.

22. The method of claim 14, wherein the specimen is metallic.

* * * * *